(12) United States Patent
Choi (10) Patent No.: US 7,921,496 B2
(45) Date of Patent: Apr. 12, 2011

(54) ELECTRIC TOOTHBRUSH

(76) Inventor: Joo A Choi, Jeollanam-do (KR)

( * ) Notice: Subject to any disclaimer, the term of this patent is extended or adjusted under 35 U.S.C. 154(b) by 1055 days.

(21) Appl. No.: 11/571,773

(22) PCT Filed: Jul. 8, 2005

(86) PCT No.: PCT/KR2005/002212
§ 371 (c)(1),
(2), (4) Date: Mar. 22, 2007

(87) PCT Pub. No.: WO2006/006808
PCT Pub. Date: Jan. 19, 2006

(65) Prior Publication Data
US 2007/0220689 A1    Sep. 27, 2007

(30) Foreign Application Priority Data

Jul. 9, 2004  (KR) .................. 10-2004-0053646

(51) Int. Cl.
*A61C 17/34*    (2006.01)
(52) U.S. Cl. ................ 15/22.2; 15/22.1; 15/22
(58) Field of Classification Search ............. 15/22.1, 15/22.2, 23; *A61C 17/22, 17/32, 17/34*
See application file for complete search history.

(56) References Cited

U.S. PATENT DOCUMENTS

| | | |
|---|---|---|
| 2,124,145 A | 7/1938 | Merkel, Jr. |
| 3,015,833 A | 1/1962 | Gilet |
| 3,258,802 A | 7/1966 | Rodriguez |
| 3,512,201 A * | 5/1970 | Taylor ............................... 15/23 |
| 3,512,202 A | 5/1970 | Taylor |
| 4,304,023 A | 12/1981 | O'Rourke |
| 4,603,448 A * | 8/1986 | Middleton et al. .............. 15/22.1 |
| 4,845,796 A | 7/1989 | Mosley |
| 5,044,035 A | 9/1991 | Barradas |
| 5,173,983 A * | 12/1992 | Le ..................................... 15/28 |
| 5,428,855 A | 7/1995 | Li |
| 5,453,644 A | 9/1995 | Yap et al. |
| 5,465,444 A | 11/1995 | Bigler et al. |
| 5,504,959 A | 4/1996 | Yukawa et al. |
| 5,846,911 A | 12/1998 | Arnoux et al. |
| 2004/0010871 A1 | 1/2004 | Nishinaka et al. |
| 2004/0168270 A1 | 9/2004 | Choi et al. |

FOREIGN PATENT DOCUMENTS

| | | |
|---|---|---|
| CN | 85 2 01346 U | 2/1986 |
| CN | 2079948 U | 7/1991 |
| CN | 2312679 Y | 4/1999 |
| DE | 199 30 294 A1 | 4/2001 |
| EP | 0 488 971 A2 | 3/1992 |
| FR | 2 662 350 A1 | 11/1991 |
| JP | 54-58472 U | 2/1993 |
| JP | 07-177932 A | 7/1995 |

(Continued)

*Primary Examiner* — Monica S Carter
*Assistant Examiner* — Stephanie Newton
(74) *Attorney, Agent, or Firm* — Leydig, Voit & Mayer, Ltd.

(57) ABSTRACT

An electric toothbrush includes a case in which a motor is installed, at least one toothbrush handle, which is installed in the case, for rotating and swinging at a predetermined angle has a brush at a tip. A power transmitter, which is installed in the case between the motor and the toothbrush handle, rotates the toothbrush handle, and a vibration generator, which is installed in the case between the motor and the toothbrush handle, reciprocates the toothbrush handle.

4 Claims, 9 Drawing Sheets

FOREIGN PATENT DOCUMENTS

| | | |
|---|---|---|
| JP | 7-213342 | 8/1995 |
| JP | 7-213342 A | 8/1995 |
| JP | 8-356 | 1/1996 |
| JP | 8-19427 A | 1/1996 |
| JP | 8-280717 A | 10/1996 |
| JP | 2003-210493 | 7/2003 |
| KR | 1990-0001638 Y1 | 3/1990 |
| KR | 1999-024570 A | 4/1999 |

\* cited by examiner

ELECTRIC TOOTHBRUSH

TECHNICAL FIELD

The present invention relates to an electric toothbrush, and more particularly, to an electric toothbrush capable of brushing teeth using a brush in a 3-D motion such as rotating and vibrating, or swinging at an angle and vibrating.

BACKGROUND ART

Proper and correct tooth brushing is an essential way to maintain oral cavity hygiene and health. One of recommendable tooth brushing methods is to clean teeth by moving a brush from the gun of teeth to the edge of the teeth while the brush is held in position on the gum. However, brushing teeth in this manner actually takes a lot of time and repeating the regular actions is a difficult job.

Considering the above inconveniences, the present inventor developed an electric toothbrush using two brush heads capable of simultaneously cleaning the inner and outer sides of teeth and filed the same as the International PCT Patent Application No. PCT/KR02/01334. The electric toothbrush cleans teeth using the brush rotating at either side of the teeth.

DISCLOSURE OF INVENTION

Technical Problem

To solve the above and/or other problems, the present invention provides an electric toothbrush which can operate to clean teeth adaptively according to tooth states while improving tooth cleaning efficiency.

The present invention provides an electric brush which can prevent brushes, that is, toothbrush bristles, from being stuck between teeth or the gums, from being damaged, and smoothly clean an engaged surface between teeth during brushing teeth.

The present invention provides an electric brush which improves accessibility to a region where a brush portion is difficult to access, increases efficiency in removing plug from the teeth, and facilitates brushing of the engaged surface and the lateral surfaces of teeth.

The present invention provides an electric brush which performs brushing by rotating, swinging at an angle, or reciprocating a brush to clean teeth.

According to an aspect of the present invention, an electric toothbrush comprises a case in which a motor is installed, at least one toothbrush handle which is installed in the case capable of rotating and swinging at a predetermined angle and has a brush formed at a tip thereof, a power transmitter which is installed in the case between the motor and the toothbrush handle and rotates the toothbrush handle, and a vibration generator which is installed in the case between the motor and the toothbrush handle and reciprocates the toothbrush handle.

In the present invention, the toothbrush handle installed in the case may be formed of an elastic material having an elastic force. The toothbrush handle may include first and second toothbrush handles which are installed parallel to each other. The electric toothbrush between the first and second toothbrush handles, the vibration generator vibrating the first and second toothbrush handles in a direction perpendicular to the lengthwise direction.

According to another aspect of the present invention, there is provided an electric toothbrush comprising: a case in which a motor is installed; first and second toothbrush handles which is installed in the case capable of rotating and has brushes formed at tips thereof; a power transmitter which is installed in the case between the motor and the first and second toothbrush handles and rotates the first and second toothbrush handles; and a vibration generator which is installed in the case between the motor and the first and second toothbrush handles and reciprocates the first and second toothbrush handles.

According to still another aspect of the present invention, there is provided an electric toothbrush comprising: a case in which a motor is installed; first and second toothbrush handles which are installed in the case capable of rotating and have first and second brushes formed at tips thereof to clean lateral sides of teeth; a third toothbrush handle which is installed in the case capable of reciprocating or swinging at a pre-determined angle and has an auxiliary brush to clean an engaged surface of the teeth; a first power transmitter which is installed in the case between the motor and the first and second toothbrush handles and rotates the first and second toothbrush handles; and a second power transmitter which rotates the third toothbrush handle using the rotational force of the motor.

BEST MODE FOR CARRYING OUT THE INVENTION

Figure 1:
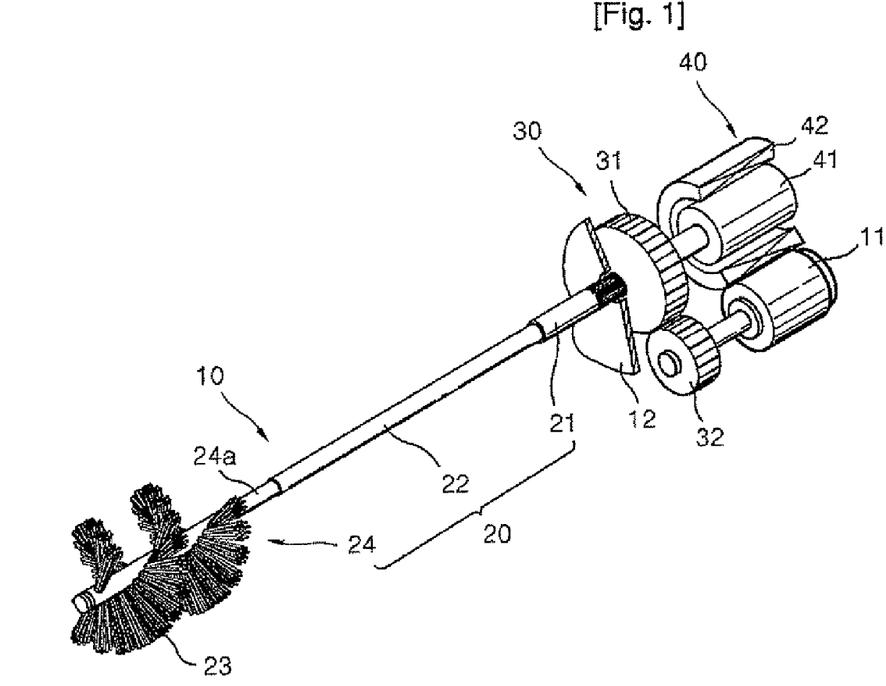
FIG. 1 is a perspective view of an electric toothbrush according to an embodiment of the present invention.

An electric toothbrush according to the present invention cleans at least one lateral side of teeth by making a brush rotate and vibrate, or swing at an angle, of which an embodiment is shown in FIG. 1. Referring to FIG. 1, an electric toothbrush 10 includes a case 12 accommodating a motor 11 and a toothbrush handle 20 installed in the case 12 to be capable of rotating and reciprocating. The toothbrush handle 20 includes a support member 21 that is rotated and vibrated by a power transmitter 30 and a vibration generator 40, respectively, a toothbrush support rod 22 assembled to/disassembled from the support member 21 and having an elastic force, and a brush 24 provided at a tip of the support rod 22 and capable of being assembled to/disassembled from the toothbrush support rod 22. The toothbrush support rod 22 is encompassed by a housing (not shown) that is fixed to the case 12, so that an oral cavity can be protected. The brush 24 includes a brush support rod 24a coupled to the toothbrush handle 20 and brush tufts 23, that is, toothbrush bristles, implanted spirally and in stripes on the brush support rod 24a.

The power transmitter 30 includes a driven gear 31 spline-coupled to the support member 21 and having its motion in the lengthwise direction of the support member 21 limited by the case 12 and a drive gear 32 engaged with the driven gear 31 and rotated by the motor 1l. The power transmitter 30 is not limited to the present embodiment and may include pulleys and belts. A pulley (not shown) supported by the support member 21 has its motion limited in the lengthwise direction of the support member 21 and can transmit power to the support member 21. In particular, the driven gear 31 and the drive gear 32 are not directly engaged with each other and a plurality of idle gears for acceleration or deceleration can be installed between the driven gear 31 and the drive gear 32. Also, a gear motor having an increased rotation torque and adjusted number of rotations is used.

Figure 2:
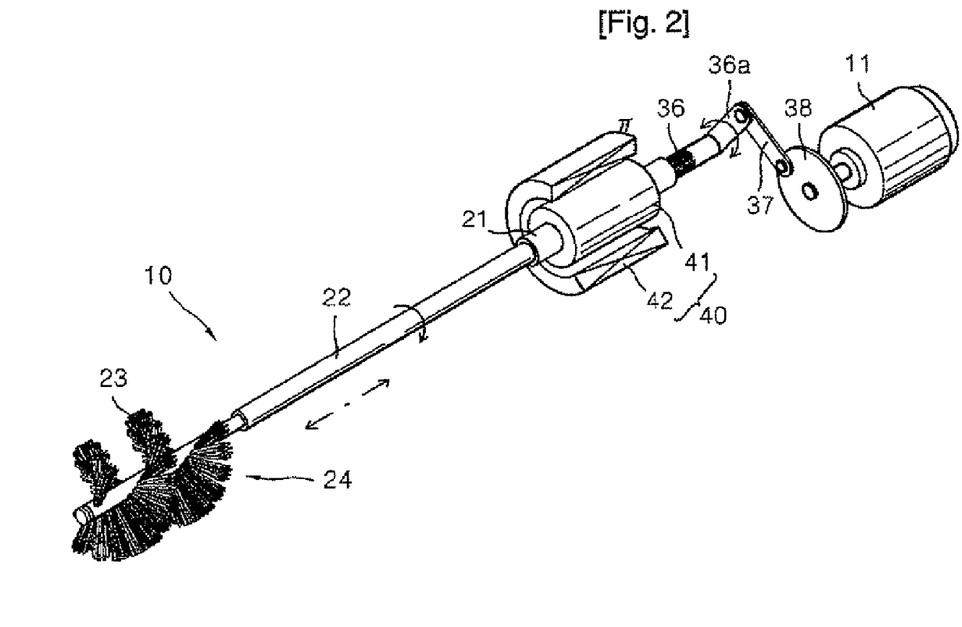
FIGS. 2 and 3 are perspective views of electric toothbrushes according to other embodiments of the present invention.

In the meantime, as shown in FIG. 2, the brush 24 for cleaning the teeth can perform a swing motion at a predetermined angle. To this end, the power transmitter 30 includes an auxiliary shaft 36 spline-coupled to the support member 21, an elongate portion 36a extending in a radial direction from the auxiliary shaft 36, and a cam 38 connected to the elongate portion 36a via a link 37 and rotated by the motor 11.

The vibration generator 40 includes a flange 41 installed at the support member 21 and a coil unit 42 installed around the outer circumferential surface of the flange 41 and allowing the flange 41 to reciprocate in the axial direction at a resonant frequency of the flange 41 when AC current is applied thereto. A spring (not shown) for providing an elastic force during the reciprocation of the support member 21 can be further provided at a tip of the support member 21.

Figure 3:
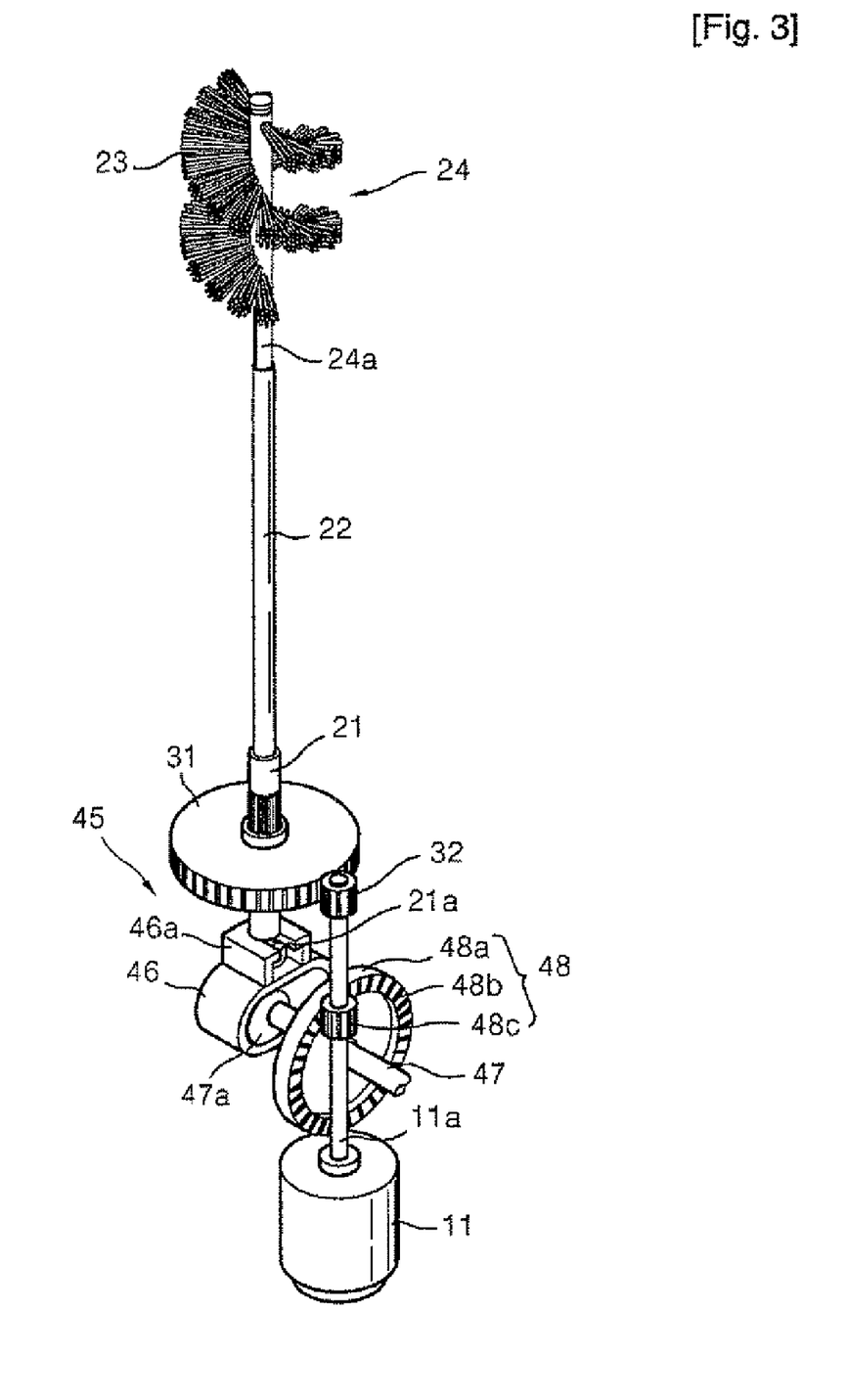
Figure 4:
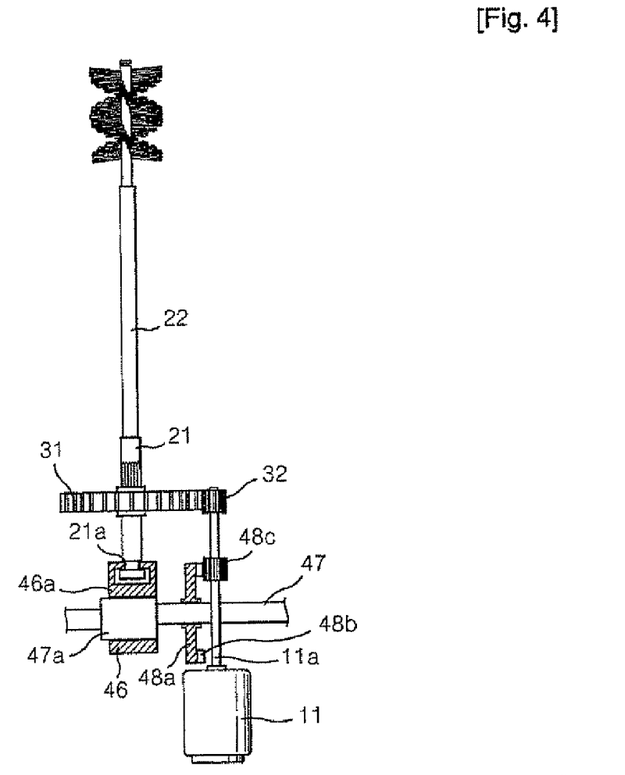
FIG. 4 is a partially cut-away side view of the electric toothbrush of FIG. 3.
Figure 5:
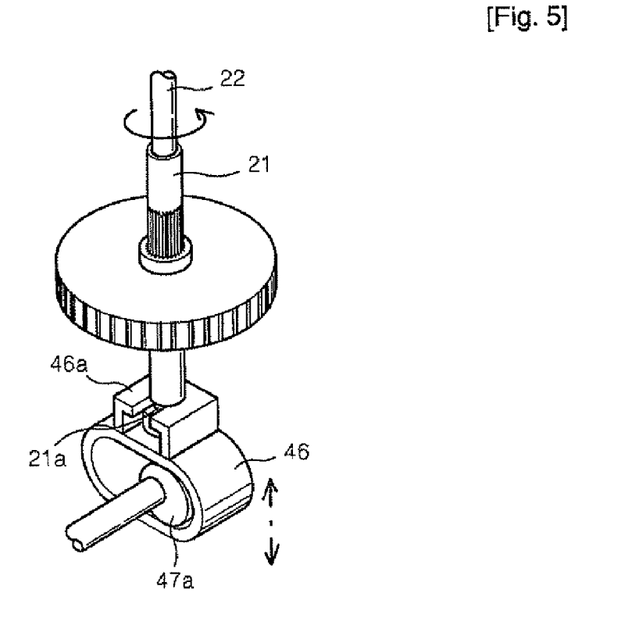
FIG. 5 is a perspective view the vibration generator of the electric toothbrush of FIG. 3.

FIGS. 3 through 5 show the vibration generator of an electric toothbrush according to another embodiment of the present invention. Referring to FIGS. 3 through 5, a vibration generator 45 according to the present embodiment includes an eccentric cam housing 46 on which a tip of the support member 21 is rotatably supported, an eccentric cam 47a coupled to the eccentric cam housing 46 and installed on a driven shaft 47, and an eccentric cam power transmitter 48 transmitting a rotational force of the motor 11 to the driven shaft 47.

The support of the support member 21 on the eccentric cam housing 46 is made as a groove 21a is formed at a tip of the support member 21 and the grooves 21a is supported by a bracket 46a formed on the eccentric cam housing 46. The eccentric cam power transmitter 48 includes an eccentric cam driven gear 48a installed on the driven shaft 47 and having a tooth portion 48b at a lateral surface thereof and an eccentric cam driving gear 48c installed on a rotation shaft 11a of the motor 11.

Although not shown in the drawings, a cover member can be installed to protect an inner wall of an oral cavity during brushing teeth.

Figure 6:
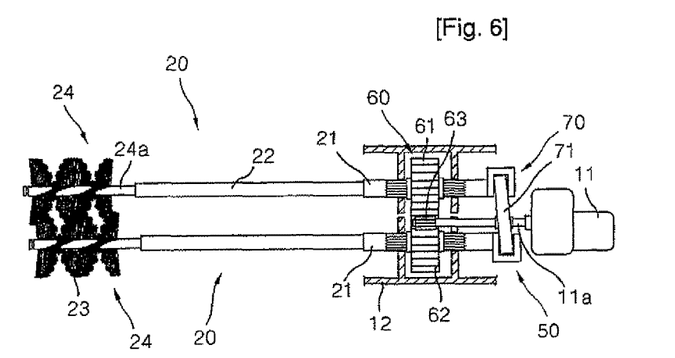
FIG. 6 is a partially cut-away side view of an electric toothbrush according to another embodiment of the present invention.
Figure 7:
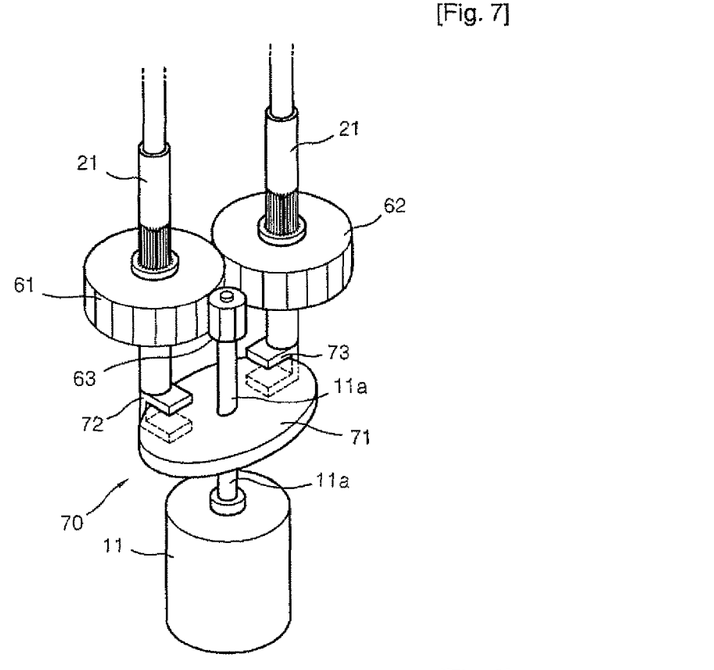
FIG. 7 is a perspective view of the power transmitter and the vibration generator of the electric toothbrush of FIG. 6.

FIGS. 6 and 7 show an electric toothbrush 50 according to another embodiment of the present invention.

Referring to FIGS. 6 and 7, the electric toothbrush 50 includes the case 12 accommodating the motor 11, first and second toothbrush handles 20, 20 installed in the case 12 to be capable of rotating and swinging at a predetermined angle, a power transmitter 60 installed in the case 12 and transmitting the rotational force of the motor 11 to the first and second support members 21, 21 of the first and second toothbrush handles 20, 20, and a vibration generator 70 reciprocating the first and second support members 21, 21. In the present embodiment, the first and second toothbrush handles 20, 20 have the same structure as that of the toothbrush handle according to the above-described embodiments.

The power transmitter 60, as shown in FIGS. 6 and 7, includes first and second driven gears 61 and 62 spline-coupled to the first and second support members 21, 21 and engaged with each other and a drive gear 63 installed on the rotation shaft 11a of motor 11 and engaged with one of the first and second driven gears 61 and 62. The first and second support members 21, 21 have polygonal sections or have guide keys formed in the lengthwise direction thereof. A hole formed in a boss of each of the first and second driven gears 61 and 62 has substantially the same shape as that of the section of each of the first and second support members 21, 21. Thus, the first and second support members 21, 21 are spline-coupled to the first and second driven gears 61 and 62 to be capable of sliding. In this case, as in the above-described embodiments, the movement of the first and second driven gears 61 and 62 in the lengthwise direction thereof must be limited by the case 12.

The vibration generator 70 making the first and second support members 21, 21 reciprocate and vibrate in the lengthwise direction thereof, as shown in FIGS. 6 and 7, includes an inclined disc 71 installed inclined at the rotation shaft 11a of the motor 11 to rotate the first and second support members 21, 21 and first and second guide members 72 and 73 installed at tips of the first and second support members 21, 21 and guide to move up and down by being coupled to the edge of the inclined disc 71. The first and second guide members 72 and 73 are inserted in the inclined disc 71 such that upper and lower edges of each of the first and second guide members 72 and 73 are supported.

Figure 8:
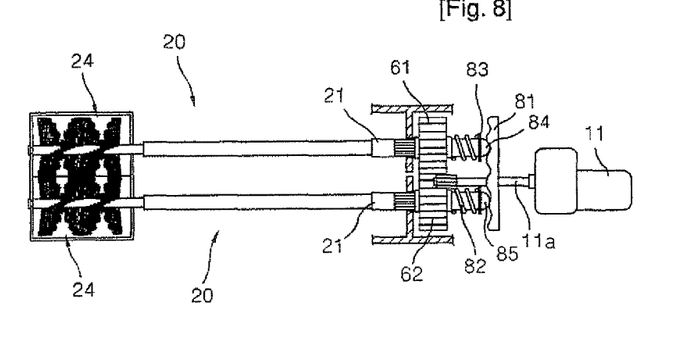
FIG. 8 is a partially cut-away side view of an electric toothbrush according to still another embodiment of the present invention.
Figure 9:
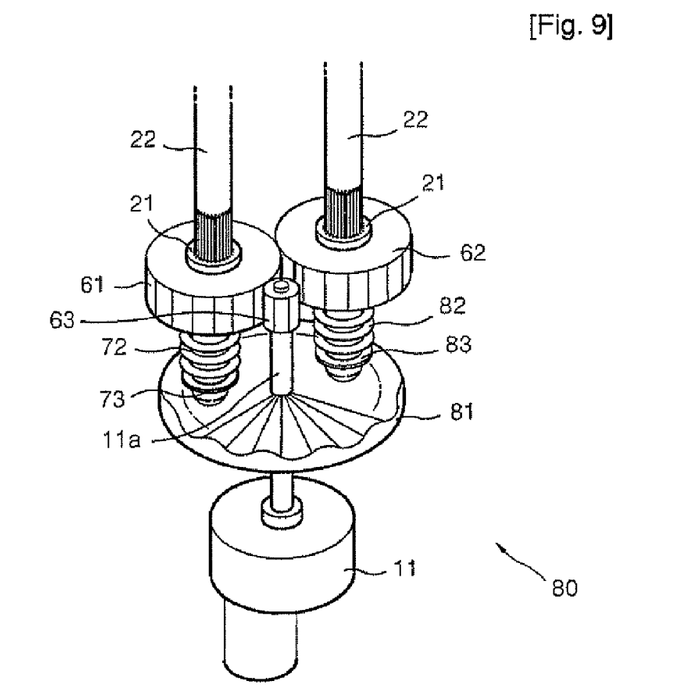
FIG. 9 is a perspective view of the power transmitter of the electric toothbrush of FIG. 8.

FIGS. 8 and 9 show a vibration generator 80 of an electric toothbrush according to another embodiment of the present invention. Referring to FIGS. 8 and 9, the vibration generator 80 includes a rotary disc 81 installed on the rotation shaft 11a of the motor 11 and having an uneven surface contacting tips of the first and second support members 21, 21 of the first and second toothbrush handles 20, 20 to reciprocate the first and second support members 21, 21 in the lengthwise direction thereof, and first and second springs 82 and 83 installed at the first and second support members 21, 21 and elastically biasing the first and second support members 21, 21 toward the rotary disc 81. First and second stoppers 84 and 85 are installed at the tips of the first and second support members 21, 21. The first and second springs 82 and 83 are respectively inserted around the first and second support members 21, 21 between the first driven gear 61 and the first stopper 84, and the second driven gear 62 and the second stopper 85. Thus, the first and second support members 21, 21 can be elastically biased toward the rotary disc 81.

Figure 10:
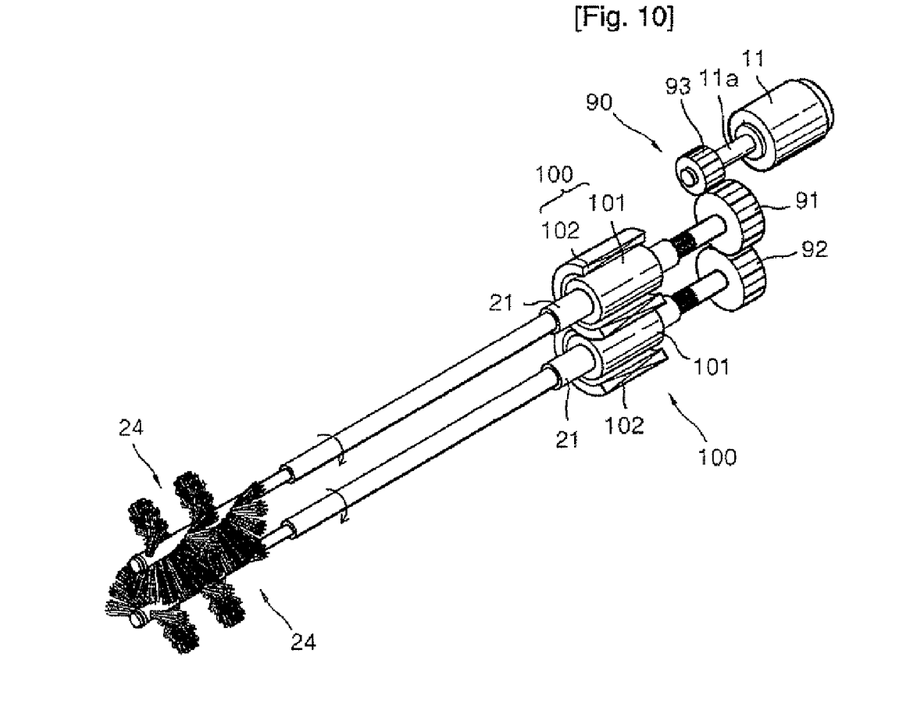
FIG. 10 is a partially cut-away perspective view of an electric toothbrush according to yet another embodiment of the present invention.

FIG. 10 shows an electric toothbrush according to another embodiment of the present invention. Elements having the same functions in the above-described embodiments are respectively identified by the same reference numerals.

Referring to FIG. 10, a power transmitter 90 for transmitting power of the motor 11 includes first and second driven gears 91 and 92 installed at the first and second support members 21, 21 and engaged with each other and a drive gear 93, installed on the rotation shaft 11a of the motor 11 and engaged with the first driven gear 91 of the first and second driven gears 91 and 92 installed at the first and second support members. The drive gear 93 and the first driven gear 91 may not be engaged directly but be engaged with each other via a plurality of idle gears.

A vibration generator 100 reciprocates the brushes 24, 24 coupled to the toothbrush support rods 22, 22 by reciprocating the first and second support members 21, 21 of the first and second toothbrush handles 20, 20. The vibration generator 100 includes flanges 101, 101 installed at the first and second support members 21, 21 and coil units 102, 102 installed around the outer circumferential surfaces of the flanges 101, 101 to be separated a predetermined distance from the Ranges 101, 101 and reciprocating the flanges 101, 101 in the axial direction at a resonant frequency when AC current is applied thereto.

Figure 11:
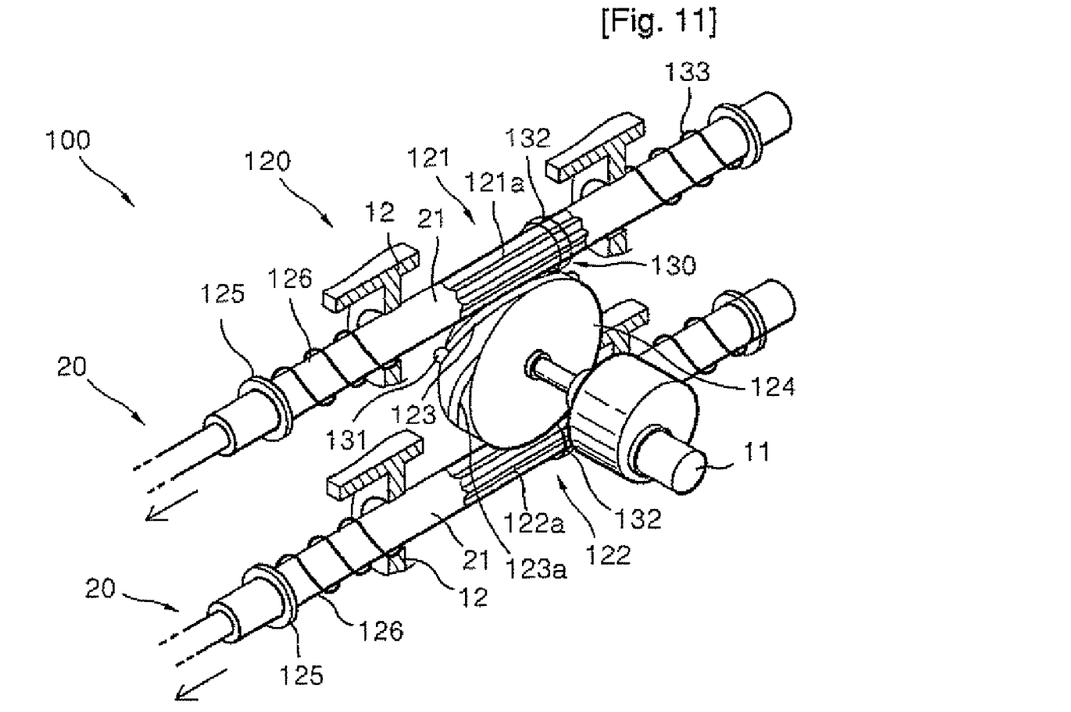
FIG. 11 is a perspective view of the power transmitter and the vibration generator of an electric toothbrush according to still yet another embodiment of the present invention.
Figure 12:
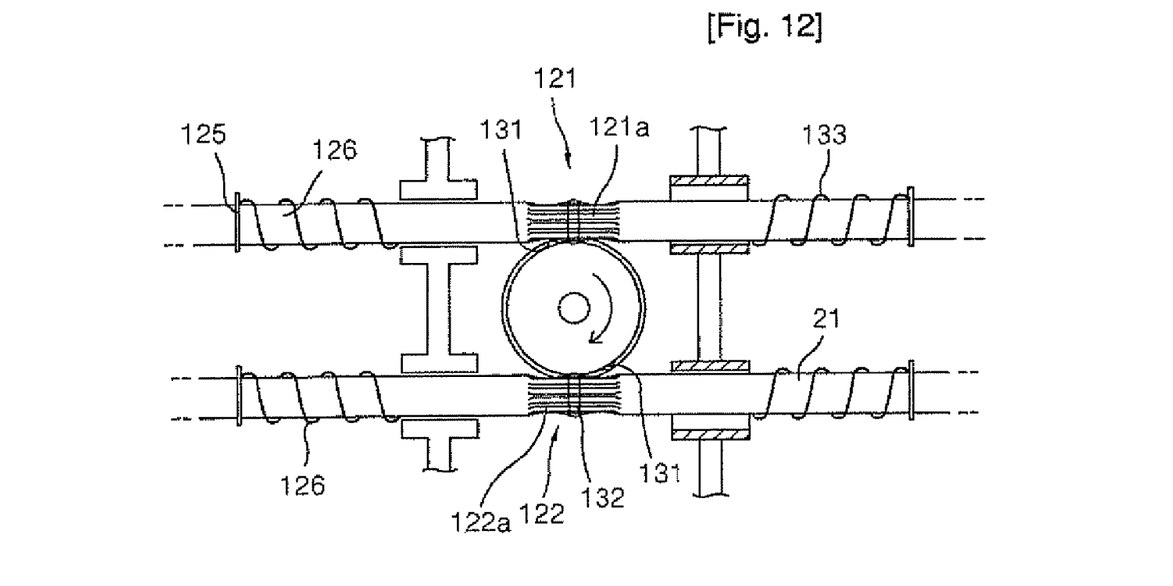
FIG. 12 is a side view of the power transmitter and the vibration generator of the electric toothbrush of FIG. 11.

FIGS. 11 and 12 show the power transmitter and the vibration generator of an electric toothbrush according to another embodiment of the present invention. Elements having the same functions in the above-described embodiments are respectively identified by the same reference numerals.

Referring to FIGS. 11 and 12, an electric toothbrush 110 includes the case 12 accommodating the motor 11 and the first and second toothbrush handles 20, 20 installed in the case 12 to be capable of rotating and having the brush 24 at the tip thereof, a power transmitter 120 installed in the case 12 between the motor 11 and the first and second toothbrush handles 20, 20 and rotating the first and second support members 21, 21 of the first and second toothbrush handles 20, 20, and a vibration generator 130 vibrating the first and second toothbrush handles 20, 20 by reciprocating the same and simultaneously vibrating the first and second toothbrush handles 20, 20 in a direction perpendicular to the lengthwise direction of the first and second toothbrush handles 20, 20.

The power generator 120 includes first and second gears 121 and 122 installed on the outer circumferential surfaces of the first and second support members 21, 21 of the first and second toothbrush handles 20, 20 and a disc 124 having at least a third gear 123 coupled to each of the first and second gears 121 and 122 and being rotated by the motor 11. The first and second gears 121 and 122 are formed on the outer circumferential surfaces of the first and second support members 21, 21 in the lengthwise direction thereof. A tooth 123a of the third gear 123 is formed inclined on the outer circumferential surface of the disc 124 to move teeth 121a and 122a of the first and second gears 121 and 122 one by one during the rotation of the disc 124. First and second hook steps 125, 125 are installed on the outer circumferential surfaces of the first and second support members 21, 21 of the first and second toothbrush handles 20, 20. First and second springs 126, 126 are provided between the first and second hook steps 125, 125 and the case 12 to elastically bias the first and second support members 21, 21 in a direction opposite to the rotational direction of the disc 124.

The vibration generator 130 generates vibration by reciprocating the first and second toothbrush handles 20, 20 during the rotation of the disc 124 and simultaneously makes the fast and second toothbrush handles 20, 20 vibrate in a direction perpendicular to the lengthwise direction thereof. The vibration generator 130 includes a rising 131 formed at the rear tip of the third gear 123, a protruding step 132 formed on each of the first and second gears 121 and 122 and contacting the rising 131, and an auxiliary spring 133 elastically biasing a tip of each of the first and second support members 21, 21 toward the outside.

Figure 13:
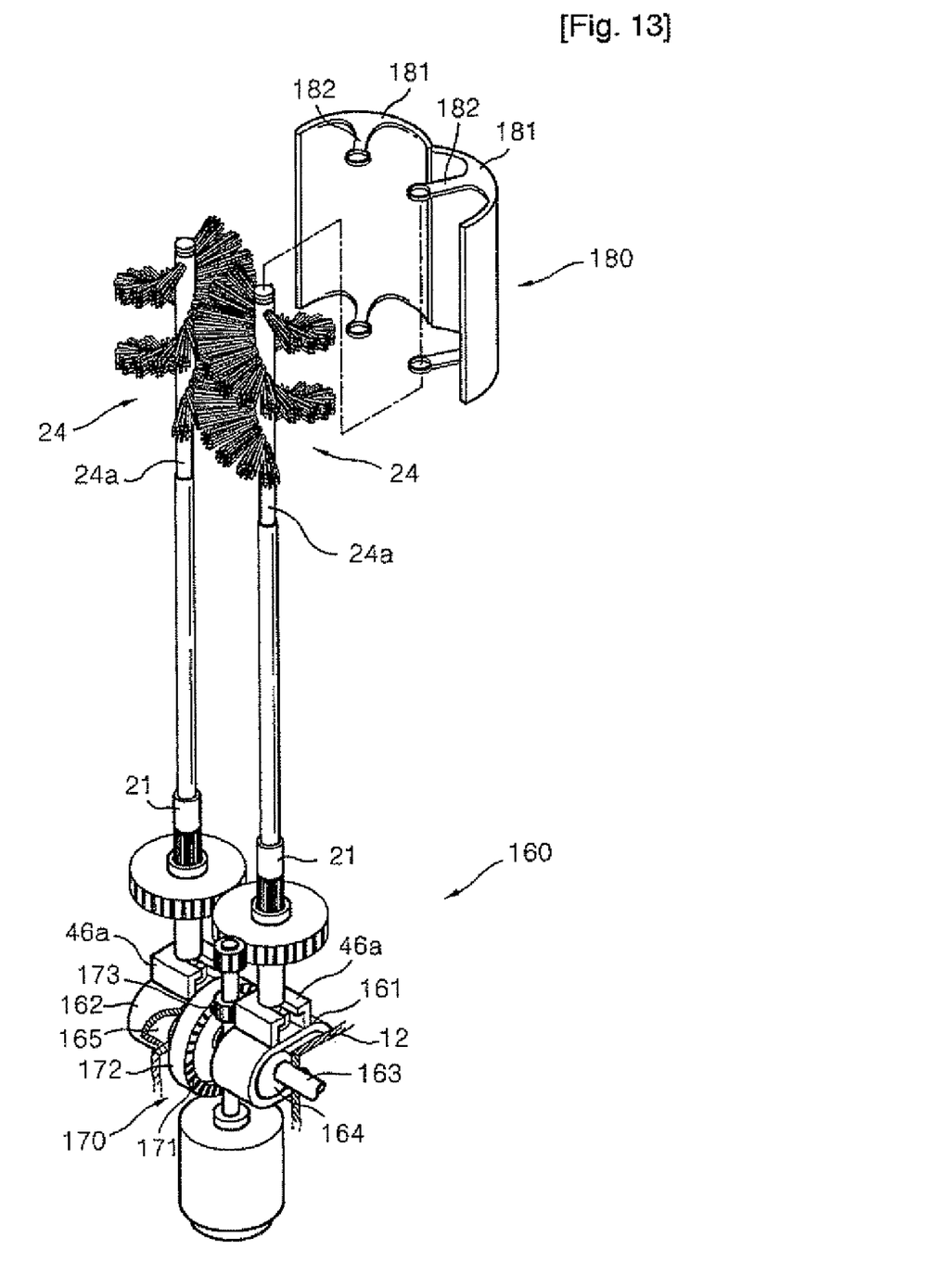
FIGS. 13 through 16 are perspective views of electric toothbrushes according to other embodiments of the present invention.

FIG. 13 shows an electric toothbrush according to another embodiment of the present invention. Elements having the same functions in the above-described embodiments are respectively identified by the same reference numerals.

Referring to FIG. 13, a vibration generator 160 includes first and second eccentric cam housings 161 and 162 supporting the tips of the first and second support members 21, 21 capable of rotating, first and second eccentric cams 164 and 165 coupled to the first and second eccentric cam housings 161 and 162 and installed on a driven shaft 163, and an eccentric cam power transmitter 170 transmitting the rotational force of the motor 11 to the driven shaft 163.

The first and second support members 21, 21 are supported by the first and second eccentric cam housings 161 and 162 such that the grooves 21a, 21a are formed at the tips of the first and second support members 21, 21 and the grooves 21a, 21a are supported by the brackets 46a, 46a formed on the first and second eccentric cam housings 161 and 161 as in the above-described embodiment.

The eccentric cam power transmitter 170 is installed at the driven shaft 163 between the first and second eccentric cam housings 161 and 162 and includes an eccentric cam driven gear 172 having a tooth portion 171 formed on the lateral side thereof and an eccentric cam drive gear 173 installed on the rotation shaft 11a of the motor 11.

A cover member 180 for protecting an inner wall of an oral cavity during tooth brushing is installed at the first and second brushes 24, 24. The cover member 180 includes semi-cylindrical members 181, 181 having sides hinge-coupled to each other and support portions 182, 182 extending from the semi-cylindrical members 181, 181 and supported by the first and second brushes 24, 24. The cover member 180 is not limited to the present embodiment and any structure capable of protecting the inside of the oral cavity during tooth brushing can be employed. The cover member 180 can be installed at the first and second brush support rod 24a, 24a or the case 12.

Figure 14:
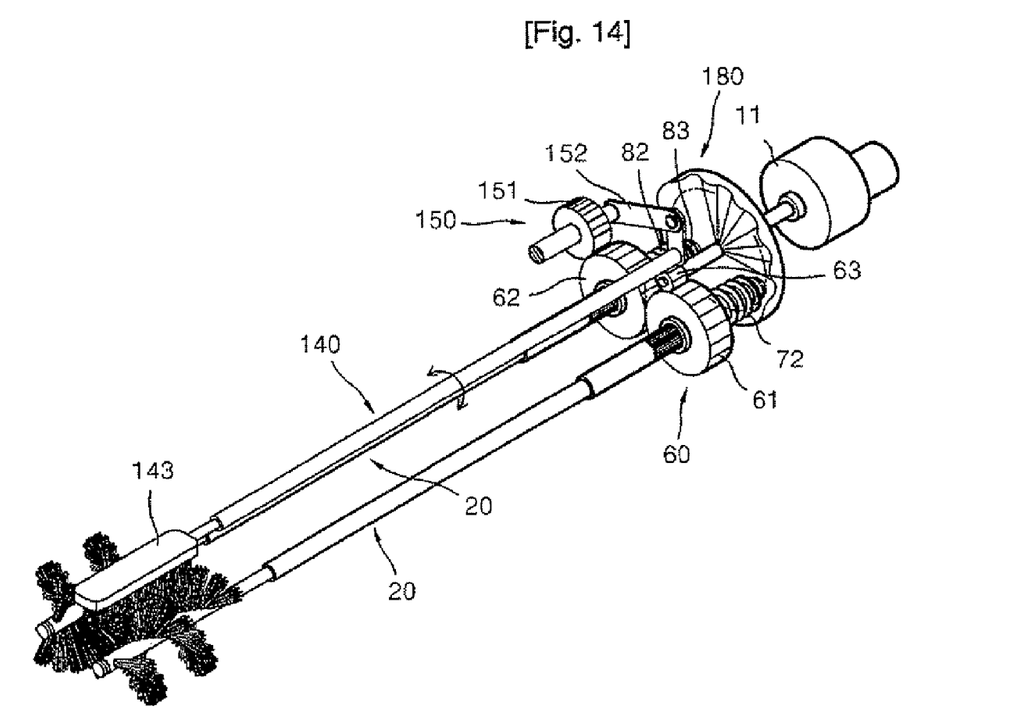
Figure 15:
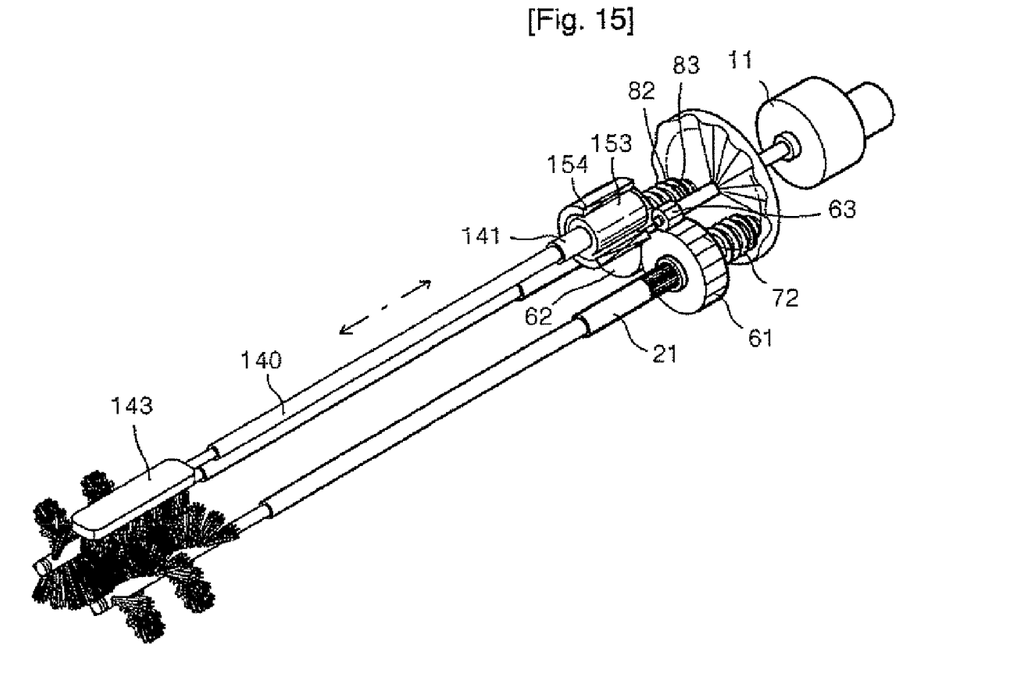

FIGS. 14 and 15 show electric toothbrushes according to other embodiments of the present invention. Referring to FIGS. 14 and 15, a third toothbrush support rod 140 is further provided, forming a triangle shape with the first and second toothbrush handles 20, 20, in which an auxiliary toothbrush portion 143 to clean the upper surface of teeth, that is, an engaged surface of the teeth is installed. Like the above-described embodiments, the power transmitter 60 for driving the first and second toothbrush handles 20, 20 and a vibration generator 80 for reciprocating the first and second toothbrush handles 20, 20 are installed in the case 12. Since the vibration generator 80 has the same structure as that of the electric toothbrush according to the above-described embodiment, a detailed description thereof is omitted herein.

The third toothbrush support rod 140 swings by receiving power from the rotation shaft ha of the motor 11 via a swing unit 150. The swing unit 150 includes an idle gear 151 engaged with the driven gear 62 and a link 152 connected to a tip of the third toothbrush 140 eccentrically with respect to the idle gear 151.

Figure 16:
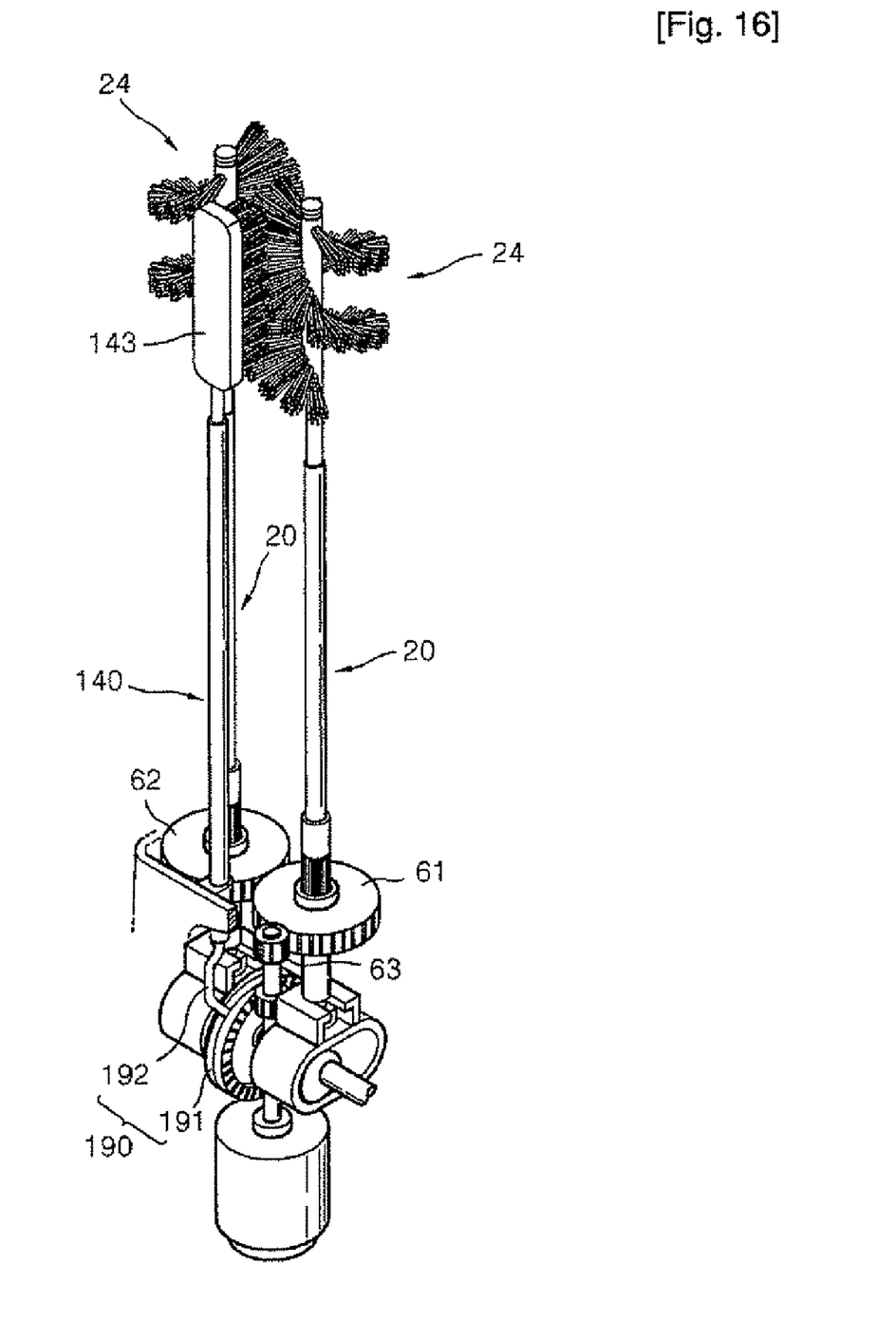

FIG. 15 shows a swing unit according to another embodiment of the present invention. Referring to FIG. 15, a flange 153 is installed on a third support member 141 of the third toothbrush support rod 140 and a coil unit 154 is installed to encompass the flange 153, thus forming a solenoid. FIG. 16 shows a swing unit 190 according to another embodiment of the present invention. Referring to FIG. 16, the swing unit 190 includes a groove 191 continuously formed inclined along the outer circumferential surface of the eccentric cam driven gear 172 and a following member 192 formed on the tip of the third toothbrush support rod 140 to follow the groove 191.

In the above-described embodiments, a lamp (not shown) to facilitate observance of the inside of an oral cavity may be further provided in the case 12. Also, in the brushes 24, 24, an array of brush tufts, that is, toothbrush bristles, is implanted spirally or in a row parallel to the lengthwise direction of the brushes 24, 24 so that the brush tufts 23, 23 are not interfered with each other even when the brushes 24, 24 of the first and second toothbrush handles 20, 20 rotate to overlap each other. Accordingly, when the brushes 24, 24 rotate to overlap each other, the volume taken by the brushes 24, 24 in an oral cavity can be greatly reduced. The cover member 80 shown in FIG. 13 may be further provided at the brushes 24, 24 to protect the inside of the oral cavity from the brushes 24, 24 during tooth brushing.

In the operation of the electric toothbrush according to the present invention configured as above, to clean teeth using the electric toothbrush 10, tooth paste is supplied to the brushes 24, 24 installed on the first and second toothbrush handles 20, 20. The motor 11 is driven when the brush turfs 23, 23, that is, toothbrush bristles, of the brushes 24, 24 of the first and second toothbrush handles 20, 20 closely contact tooth. In doing so, as the brushes 24, 24 of the first and second toothbrush handles 20, 20 rotate, both lateral sides of the teeth are cleaned. At this time, since the first and second toothbrush handles 20, 20 are reciprocated by the vibration generator, the brushes 24, 24 reciprocate with respect to the teeth so that tooth cleaning efficiency is improved. That is, as shown in FIG. 1, the flange 41 is reciprocated as a predetermined electric potential is applied to the coil unit 42 of the vibration generator 40, thus reciprocating the brush 24 with respect to the teeth. In this process, since to the support member 21 is spline-coupled to the driven gear 31 that is rotated by the motor 11, the support member 21 can smoothly reciprocate.

In the vibration generator, when the first and second toothbrush support rods are installed at the edge of the inclined disc 71 as shown m FIG. 6, or the rotary disc 81 having the uneven surface that the tips of the first and second toothbrush support rods contact is installed as shown in FIG. 8, as the inclined disc 71 or the rotary disc 81 is rotated by the motor 11, the toothbrushes are reciprocated. Also, as shown in FIG. 13, the first and second toothbrush handles 20, 20 are reciprocated as the rotational force of the motor 11 is transmitted to the driven shaft 163 by the eccentric cam power transmitter 170 and the first and second eccentric cams 164 and 165 installed on the driven shaft 163 rotate in the first and second eccentric cam housings 161 and 162.

As shown in FIGS. 14 through 16, since the electric toothbrush includes the third toothbrush support rod 140 that rotates and swings to clean the engaged surface and the auxiliary toothbrushes are installed at the tip of the third toothbrush support rod 140, the efficiency in cleaning teeth can be improved.

INDUSTRIAL APPLICABILITY

As described above, in the electric toothbrush according to the present invention, since the brush can rotate and swings at a predetermined angle and simultaneously reciprocates, the efficiency in cleaning can be improved. Also, the number of revolutions of the toothbrush support rod can be relatively reduced, the gums can be protected. Further, since the lamp is installed on the case, the oral cavity can be observed during or after cleaning teeth.

The invention claimed is:
1. An electric toothbrush comprising:
   a motor having a rotating shaft;
   a case in which the motor is located;
   at least two toothbrush handles located in the case for rotating and having brushes at tips of the at least two toothbrush handles;
   a power transmitter located in the case between the motor and the at least two toothbrush handles and rotating the at least two toothbrush handles; and
   a vibration generator located in the case, between the motor and the at least two toothbrush handles, and reciprocating the at least two toothbrush handles, wherein the vibration generator includes an eccentric cam power transmitter which comprises
      first and second eccentric cam housings supporting the tips of the at least two toothbrush handles,
      first and second eccentric cams coupled to the first and second eccentric cam housings and located on a driven shaft,
      an eccentric cam driven gear located on the driven shaft between the first and second eccentric cam housings and having a tooth portion at a side surface, and
      an eccentric cam drive gear located on the rotating shaft of the motor.
2. The electric toothbrush of claim 1, wherein the power transmitter comprises:
   driven gears which are spline-coupled to support members of the at least two toothbrush handles and engaged with each other; and
   a drive gear which is engaged with one of the driven gears and driven by the motor.
3. The electric toothbrush of claim 1, wherein the at least two toothbrush handles are elastic.
4. The electric toothbrush of claim 1, including a cover member which protects an inner wall of an oral cavity during tooth cleaning by encompassing part of the brushes.

* * * * *